United States Patent
Bor et al.

(10) Patent No.: US 12,336,938 B2
(45) Date of Patent: Jun. 24, 2025

(54) ABLATION SYSTEMS AND METHODS FOR TREATING PRESBYOPIA

(71) Applicant: Alcon Inc., Fribourg (CH)

(72) Inventors: Zsolt Bor, San Clemente, CA (US); Mario Klafke, Mainaschaff (DE); Johannes Krause, Nuremberg (DE); Keith Watanabe, Irvine, CA (US)

(73) Assignee: ALCON INC., Fribourg (CH)

( * ) Notice: Subject to any disclaimer, the term of this patent is extended or adjusted under 35 U.S.C. 154(b) by 161 days.

(21) Appl. No.: 17/643,851

(22) Filed: Dec. 13, 2021

(65) Prior Publication Data
US 2022/0192883 A1    Jun. 23, 2022

Related U.S. Application Data (60) Provisional application No. 63/128,024, filed on Dec. 19, 2020.

(51) Int. Cl.
*A61F 9/008* (2006.01)
(52) U.S. Cl.
CPC ............ *A61F 9/00808* (2013.01); *A61F 2009/00895* (2013.01)
(58) Field of Classification Search
CPC ........ A61F 9/00808; A61F 2009/00895; A61F 2009/00872; A61F 9/00827; A61F 2009/00897
See application file for complete search history.

(56) References Cited

U.S. PATENT DOCUMENTS

| | | | |
|---|---|---|---|
| 5,533,997 A | | 7/1996 | Ruiz |
| 6,033,075 A | * | 3/2000 | Fujieda ............... A61B 3/107 351/212 |
| 2001/0031959 A1 | | 10/2001 | Rozakis et al. |
| 2004/0085513 A1 | | 5/2004 | Tamayo et al. |
| 2007/0002274 A1 | | 1/2007 | Somani |
| 2009/0051876 A1 | | 2/2009 | Seiler |
| 2009/0234336 A1 | * | 9/2009 | Chernyak ............ A61F 9/008 606/5 |

(Continued)

FOREIGN PATENT DOCUMENTS

| | | |
|---|---|---|
| EP | 3120808 A1 | 1/2017 |
| WO | 2012054586 A2 | 4/2012 |
| WO | 2014087250 A2 | 6/2014 |

OTHER PUBLICATIONS

Attebo et al., "Refractive Errors in an Older Population: the Blue Mountains Eye Study", Ophthalmology, Jun. 1, 1999, vol. 106, Issue 6., p. 1066-1072.

(Continued)

*Primary Examiner* — Mark W. Bockelman (57) ABSTRACT

According to certain embodiments, an ophthalmic surgical system for treating presbyopia comprises controllable components and a computer. The controllable components comprise a light source that generates a light beam and a scanner that directs a focal point of the light beam. The computer determines an ablation profile to remove tissue from a central region and a peripheral region of a cornea of a first eye of a pair of eyes. The ablation profile is designed to remove tissue from the central region to yield a protrusion to provide for near-vision, and to remove tissue from the peripheral region to correct to emmetropia.

18 Claims, 4 Drawing Sheets

(56) References Cited

U.S. PATENT DOCUMENTS

| | | |
|---|---|---|
| 2011/0106066 A1 | 5/2011 | Bor |
| 2011/0190743 A1 | 8/2011 | Seiler et al. |
| 2012/0059465 A1* | 3/2012 | Brady ................ A61F 9/00838 623/6.39 |
| 2012/0249950 A1 | 10/2012 | Dai et al. |
| 2013/0190735 A1 | 7/2013 | Hohla et al. |
| 2014/0100556 A1* | 4/2014 | Odrich ................ A61F 9/00817 606/5 |
| 2017/0143544 A1 | 5/2017 | Holliday |
| 2018/0318134 A1* | 11/2018 | Motwani .................. A61B 3/14 |
| 2018/0333302 A1 | 11/2018 | Walter et al. |
| 2021/0321869 A1 | 10/2021 | Bor |
| 2021/0369105 A1 | 12/2021 | Bor |

OTHER PUBLICATIONS

Dierick et al. "Is the corneal contour influenced by a tension in the superficial epithelial cells? A new hypothesis" Refract Corneal Surg. Jan.-Feb. 1992; 8(1):54-9.

Juhasz, T. et al., "Corneal Refractive Surgery with Femtosecond Lasers", IEEE Journal of Selected Topics in Quantum Electronics, 1999, vol. 5, No. 4, 902-910.

Lang el al. "Structural Changes Induced by a Corneal Shape-Changing Inlay, Deduced From Optical Coherence Tomography and Wavefront Measurements", Investigative Ophthalmology & Visual Science, Jul. 2016, vol. 57, No. 9, OCT154-OCT161.

Whitman et al, "Treatment of Presbyopia in Emmetropes Using a Shape-Changing Corneal Inlay: One-Year Clinical Outcomes", Ophthalmology, Mar. 1, 2016, vol. 123, Issue 3, p. 466-475.

* cited by examiner

ABLATION SYSTEMS AND METHODS FOR TREATING PRESBYOPIA

TECHNICAL FIELD

The present disclosure relates generally to ophthalmic surgical systems and methods, and more particularly to ablation systems and methods for treating presbyopia.

BACKGROUND

The lens of the eye changes shape to focus light onto the retina so you can see objects both near and far. When you are young, the lens is soft and flexible, easily changing shape. Presbyopia occurs typically after age 40, when the lens becomes more rigid and cannot change shape as easily. This causes the eye to focus light behind rather than onto the retina when looking at close objects, reducing near-vision ability.

There are approximately 1.7 billion presbyopic people worldwide, and approximately one-third of the population of the United States is presbyopic. Treatment for presbyopia includes lenses (e.g., glasses and contact lenses), implants (e.g., intraocular lenses (IOLs), scleral implants, and corneal inlays), and multifocal refractive surgery. However, current treatments fail to provide satisfactory results in certain situations.

BRIEF SUMMARY

In certain embodiments, an ophthalmic surgical system for treating presbyopia comprises controllable components and a computer. The controllable components comprise a light source that generates a light beam and a scanner that directs a focal point of the light beam. The computer determines an ablation profile to remove tissue from a central region and a peripheral region of a cornea of a first eye of a pair of eyes. The ablation profile is designed to remove tissue from the central region to yield a protrusion to provide for near-vision, and to remove tissue from the peripheral region to correct to emmetropia. The computer instructs one or more of the controllable components to ablate the cornea of the first eye according to the ablation profile.

Embodiments may include none, one, some, or all of the following features:

The protrusion may have any suitable dimensions. For example, the protrusion may be spherical, with a diameter of 0.5 to 4 millimeters, and/or with a height of 3 to 50 micrometers, such as 20 to 40 micrometers.

If the peripheral region is designed to treat myopia, the ablation profile removes a thicker portion of the cornea at an inner portion of the peripheral region than at an outer portion of the peripheral region.

If the peripheral region is designed to treat hyperopia, the ablation profile removes a thicker portion of the cornea at an outer portion of the peripheral region than at an inner portion of the peripheral region.

If the first eye of the pair of eyes is non-dominant, and a second eye of the pair of eyes is dominant, the computer may determine a second ablation profile designed to correct the second eye to emmetropia, and instruct one or more of the controllable components to ablate the cornea of the second eye according to the second ablation profile.

The computer may generate a focal spot pattern corresponding to the ablation profile, and align the focal spot pattern relative to a visual axis to ablate the cornea.

The computer may generate a focal spot pattern corresponding to the ablation profile, a point of the focal spot pattern designated to be aligned with a visual axis of the eye; determine the visual axis of the eye; and align the point of the focal spot pattern relative to the visual axis to ablate the cornea.

In certain embodiments, a method for treating presbyopia, comprises: generating, by a light source of a plurality of controllable components, a light beam; directing, by a scanner of the plurality of controllable components, a focal point of the light beam; determining, by a computer, an ablation profile to remove tissue from a central region and a peripheral region of a cornea of a first eye of a pair of eyes, the ablation profile designed to remove tissue from the central region to yield a protrusion to provide for near-vision, the ablation profile designed to remove tissue from the peripheral region to correct to emmetropia; and instructing, by the computer, one or more of the controllable components to ablate the cornea of the first eye according to the ablation profile.

Embodiments may include none, one, some, or all of the following features:

The protrusion may have any suitable dimensions. For example, the protrusion may be spherical, with a diameter of 0.5 to 4 millimeters, and/or with a height of 3 to 50 micrometers, such as 20 to 40 micrometers.

If the peripheral region is designed to treat myopia, the ablation profile removes a thicker portion of the cornea at an inner portion of the peripheral region than at an outer portion of the peripheral region.

If the peripheral region is designed to treat hyperopia, the ablation profile removes a thicker portion of the cornea at an outer portion of the peripheral region than at an inner portion of the peripheral region.

If the first eye of the pair of eyes is non-dominant, and a second eye of the pair of eyes is dominant, the method may further comprise: determining, by the computer, a second ablation profile designed to correct the second eye to emmetropia; and instructing, by the computer, one or more of the controllable components to ablate the cornea of the second eye according to the second ablation profile.

The method may further comprise: generating, by the computer, a focal spot pattern corresponding to the ablation profile; and aligning, by the computer, the focal spot pattern relative to a visual axis to ablate the cornea.

The method may further comprise: generating, by the computer, a focal spot pattern corresponding to the ablation profile, a point of the focal spot pattern designated to be aligned with a visual axis of the eye; determining, by the computer, the visual axis of the eye; and aligning, by the computer, the point of the focal spot pattern relative to the visual axis to ablate the cornea.

In certain embodiments, an ophthalmic surgical system for treating presbyopia comprises controllable components and a computer. The controllable components comprise a light source that generates a light beam and a scanner that directs a focal point of the light beam. The computer determines an ablation profile to remove tissue from a central region and a peripheral region of a cornea of a first eye of a pair of eyes. The first eye of the pair of eyes is non-dominant, and the second eye of the pair of eyes is dominant. The ablation profile is designed to remove tissue from the central region to yield a protrusion to provide for near-vision. The protrusion is spherical with a diameter of 0.5 to 4 millimeters and with a height of 3 to 50 micrometers. The ablation profile is designed to remove tissue from the peripheral region to correct to emmetropia. If the peripheral region is designed to treat myopia, the ablation profile removes a thicker portion of the cornea at an inner portion of the peripheral region than at an outer portion of the peripheral region. If the peripheral region is designed to treat hyperopia, the ablation profile removes a thicker portion of the cornea at an outer portion of the peripheral region than at an inner portion of the peripheral region. The computer generates a focal spot pattern corresponding to the ablation profile, a point of the focal spot pattern designated to be aligned with a visual axis of the eye; determines the visual axis of the eye; aligns the point of the focal spot pattern relative to the visual axis to ablate the cornea; and instructs one or more of the controllable components to ablate the cornea of the first eye according to the ablation profile. The computer determines a second ablation profile designed to correct the second eye to emmetropia; and instructs one or more of the controllable components to ablate the cornea of the second eye according to the second ablation profile.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, an ophthalmic surgical system ablates a first eye of a pair of eyes to treat presbyopia. The system ablates tissue from central and peripheral regions of the cornea of the eye. The remaining tissue has a protrusion in the central region. The central region of the resulting cornea provides for near vision, and the peripheral region provides for far vision. In certain embodiments, the first eye is non-dominant. The system may ablate the second eye to correct the second eye to emmetropia.

Figure 1:
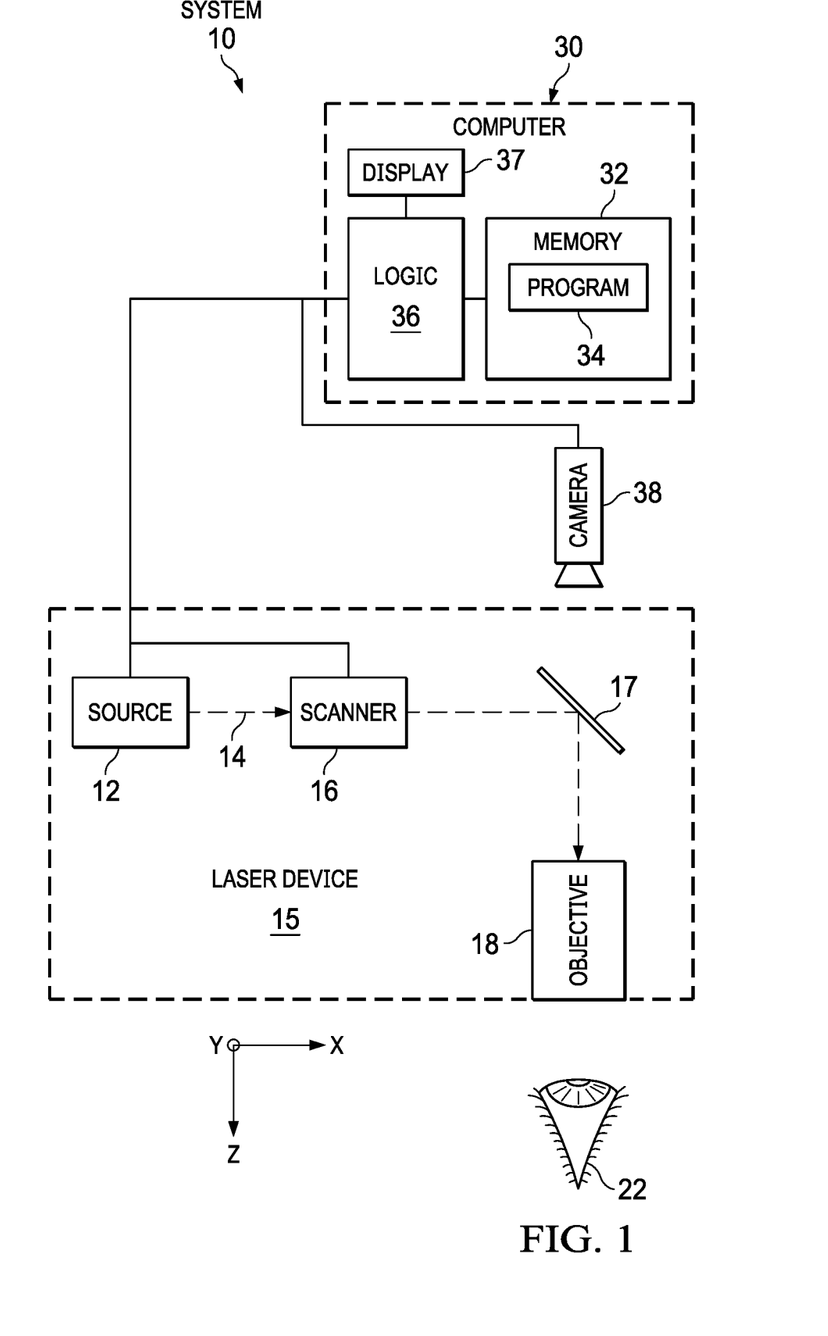
FIG. 1 illustrates an example of an ophthalmic laser ablation system that ablates the corneal tissue of an eye to treat presbyopia, according to certain embodiments.

FIG. 1 illustrates an example of an ophthalmic laser ablation system 10 that ablates the corneal tissue of eye 22 to treat presbyopia, according to certain embodiments. In the illustrated example, system 10 includes a laser device 15, a camera 38, and a control computer 30, coupled as shown. Laser device 15 includes controllable components, such as a light source (e.g., a laser source 12), a scanner 16, one or more optical elements 17, and/or a focusing objective 18, coupled as shown. Computer 30 includes logic 36, a memory 32 (which stores a computer program 34), and a display 37, coupled as shown. For ease of explanation, the following xyz-coordinate system is used: The z-direction is defined by the propagation direction of the laser beam, and the xy-plane is orthogonal to the propagation direction. Other suitable xyz-coordinate systems may be used.

As an overview, laser source 12 generates a laser beam, and scanner 16 directs the focal point of the laser beam to ablate tissue from eye 22. Computer 30 determines an ablation profile to remove tissue from a central region and a peripheral region of the cornea. The ablation profile is designed to: remove tissue from the central region to yield a protrusion to provide for near-vision, and remove tissue from the peripheral region to correct to emmetropia. Computer 30 instructs one or more of the controllable components of system 10 to ablate the cornea according to the ablation profile.

Turning to the parts of system 10, a light source generates a light beam that ablates tissue of eye 22 according to a focal spot pattern. The light beam may have a wavelength of, e.g., less than 300 nm. In the illustrated example, the light source is a laser source 12 that generates a laser beam that ablates tissue of eye 22 according to a laser focal spot pattern. Laser source 12 may be an excimer, solid-state, or other suitable laser. A focal spot pattern may define x and y coordinates for positions at which laser radiation pulses are to be directed. The focal spot pattern may be determined from an ablation profile, which indicates the volume of tissue to be removed at particular x, y positions of the cornea. Given the volume of tissue ablated per pulse, the number of pulses to be directed at an x, y position can be calculated from the volume of tissue defined by the ablation profile.

Scanner 16 laterally directs the focal point of the laser beam. The lateral direction refers to directions orthogonal to the direction of beam propagation, i.e., the x, y directions. Scanner 16 may laterally direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam towards a point of eye 22. In the example, focusing objective 18 is an objective lens, e.g., an f-theta objective.

Camera 38 records images of the eye 22. Examples of camera 38 include a video, an optical coherence tomography, or an eye-tracking camera. Camera 38 delivers image data, which represent recorded images of the eye 22, to computer 30. Computer 30 may carry out image processing on the image data to monitor ablation of eye 22.

Computer 30 controls components of system 10 in accordance with computer program 34. For example, computer 30 controls components (e.g., laser source 12, scanner 16, optical elements 17, and/or focusing objective 18) to focus the laser beam of laser device 15 at eye 22 and to ablate at least a portion of eye 22 according to an ablation profile. In certain embodiments, computer 30 generates a focal spot pattern corresponding to the ablation profile. Computer 30 may generate a focal spot pattern by determining the focal spots corresponding to the tissue removed according to the ablation profile. The ablation profile indicates the volume of tissue to be removed at particular x, y positions of the cornea. Given the volume of tissue ablated per pulse, the number of pulses to be directed at an x, y position can be calculated from the volume of tissue defined by the ablation profile.

In certain embodiments, computer 30 determines an ablation profile to remove tissue from a central region and a peripheral region of the cornea. The ablation profile is designed to: remove tissue from the central region to yield a protrusion to provide for near-vision, and remove tissue from the peripheral region to correct to emmetropia. In other embodiments, computer 30 may determine the ablation profile by retrieving the profile from memory 32, where the ablation profile was determined as described above.

In certain embodiments, computer 30 aligns the focal spot pattern relative to an axis of the eye (e.g., optical or visual axis) to ablate the cornea. In certain cases, a particular point of the focal spot pattern is designated to be aligned with the axis. Computer 30 may align the point relative to the axis by receiving a measurement or coordinates (e.g., xy coordinates) identifying the location of the axis, and then aligning the point at the axis. In certain embodiments, computer 30 may determine the xy coordinates of the visual axis according to methods described in US Patent Applications Nos. 63/010,293 (filed 15 Apr. 2020) and 63/033,327 (filed 2 Jun. 2020). Computer 30 may then align the particular point with the xy position of the visual axis.

In certain embodiments, computer 30 treats a pair of eyes. A first eye (e.g., the non-dominant eye) is treated according to the ablation profile with the protrusion for near-vision correction, and a second eye (e.g., the dominant eye) is treated with a profile that corrects to emmetropia. In the embodiments, the dominant or non-dominant eye may be the first or second eye.

Figure 2:
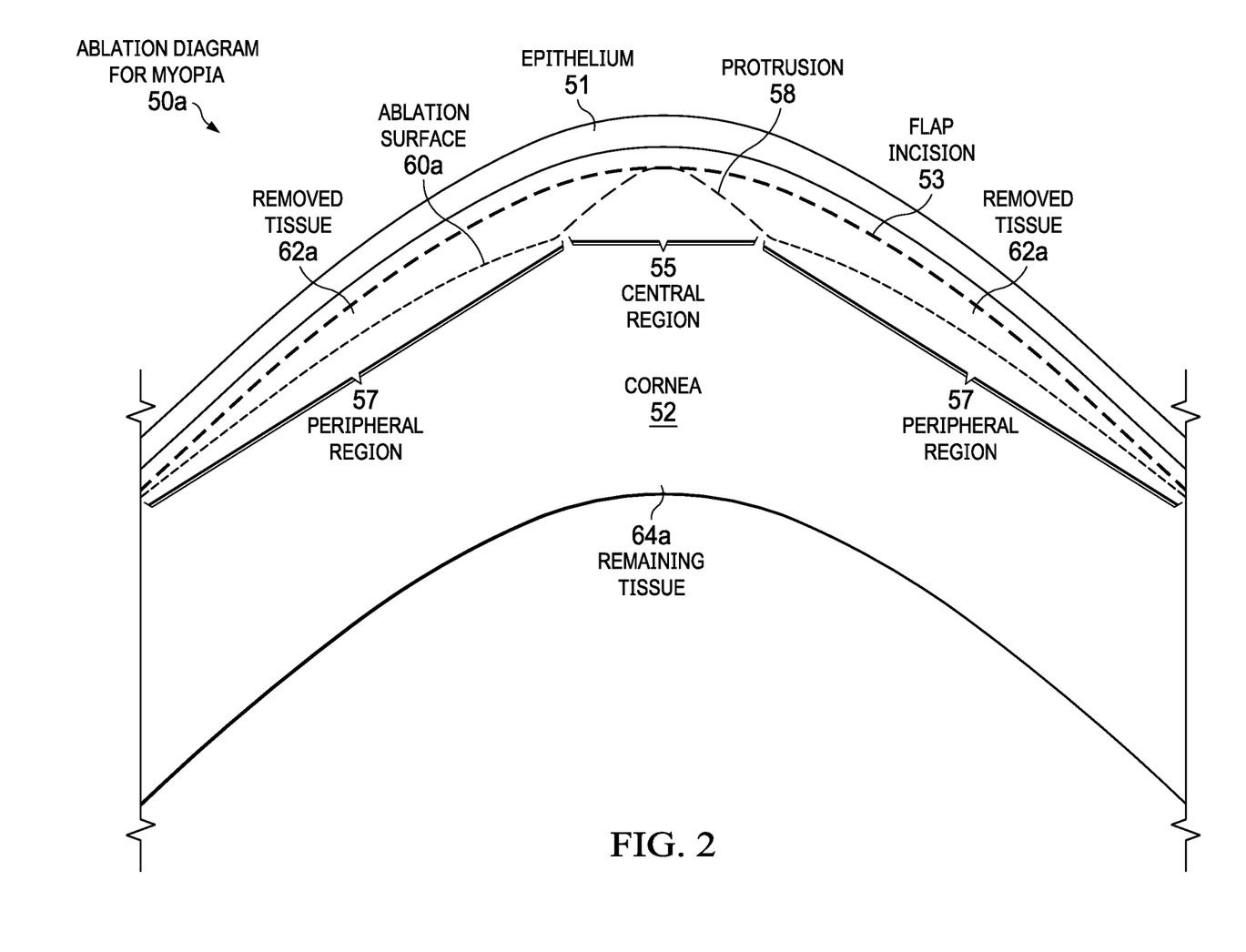
FIG. 2 illustrates an ablation diagram that the system of FIG. 1 may use to treat myopic presbyopia.
Figure 3:
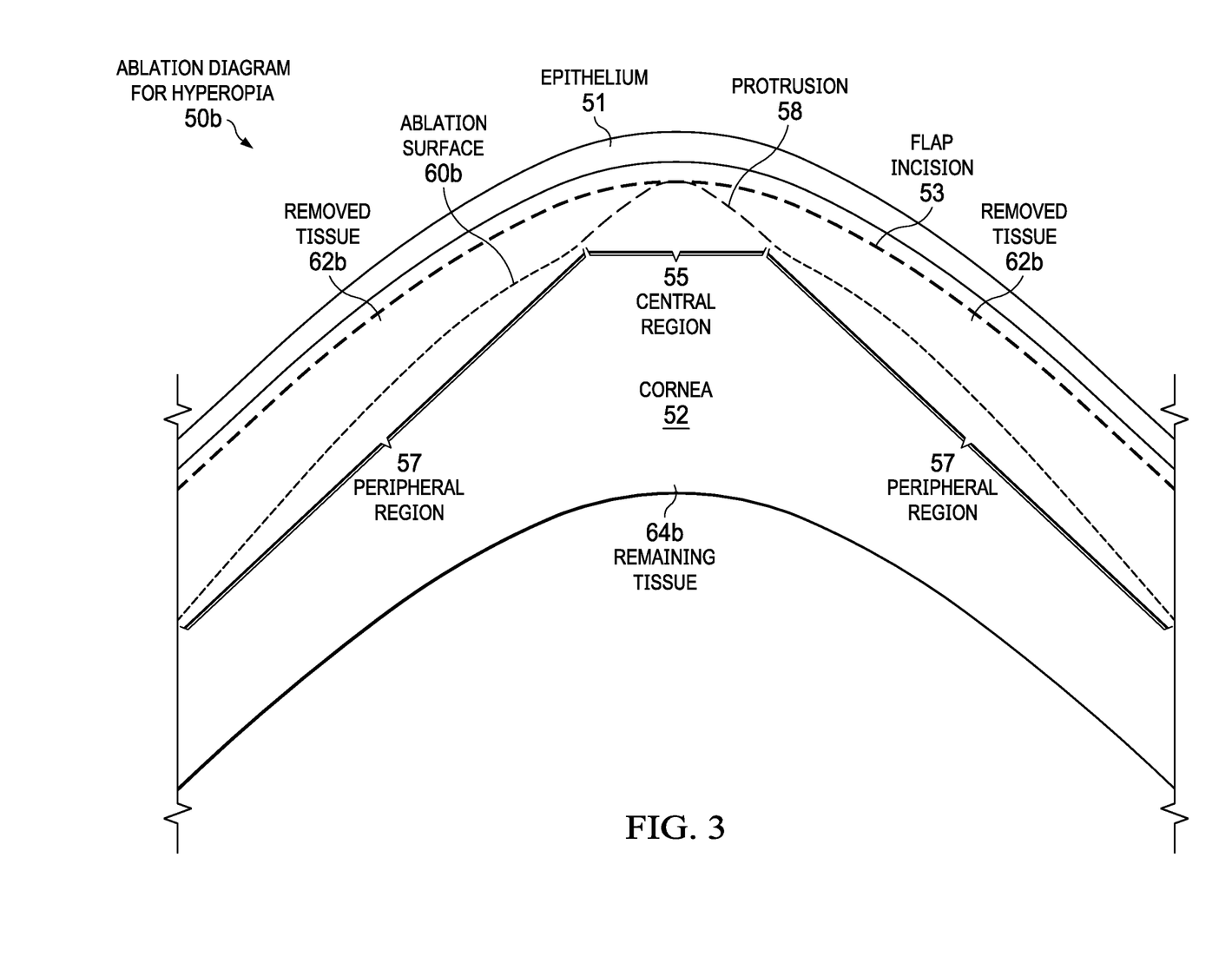
FIG. 3 illustrates an ablation diagram that the system of FIG. 1 may use to treat hyperopic presbyopia.

FIGS. 2 and 3 illustrate examples of ablation diagrams 50 (50a, 50b) that system 10 of FIG. 1 may use to treat myopic presbyopia and hyperopic presbyopia, respectively. An ablation diagram 50 may be used for any suitable refractive procedure that shapes the cornea, e.g., laser-assisted in situ keratomileusis (LASIK) or photorefractive keratectomy (PRK). In the examples, ablation diagrams 50 (50a, 50b) are used for LASIK. In the examples, an ablation diagram 50 shows epithelium 51 and cornea 52. Cornea 52 has a central region 55 and a peripheral region 57. Central region 55 is substantially centered about an axis (e.g., visual or optical) of the eye, and peripheral region 57 extends from central region 55 towards the edge of the cornea.

A flap incision 53 indicates the incision formed to create a LASIK flap. Removed tissue 62 (62a, 62b) indicates the tissue ablated according to the ablation profile, and remaining tissue 64 (64a, 64b) indicates the tissue remaining after ablation. An ablation surface 60 (60a, 60b) indicates the stromal surface remaining after the tissue has been ablated according to the ablation profile.

Ablation surface 60 of central region 55 and peripheral region 57 may have any suitable size and/or shape, and computer 30 may determine the dimensions of ablation surface 60 in any suitable manner. In certain embodiments, computer 30 may receive information describing the refractive correction, and determine the dimensions from the information.

In the embodiments, computer 30 may calculate the dimensions of peripheral region 57 from information describing far-vision correction. In certain examples, removal of a thickness of 14 to 18 micrometers corresponds to approximately 1 diopter of correction. The location of the thickness (e.g., center or periphery) depends on whether the correction is for myopia or hyperopia. Generally, myopia treatment removes a thicker portion of the corneal at an inner portion of the peripheral region than at an outer portion (e.g., ablation diagram 50a of FIG. 2), and hyperopia treatment removes a thicker portion of the corneal at an outer portion of the peripheral region than at an inner portion (e.g., ablation diagram 50b of FIG. 3). In certain embodiments, ablation of peripheral region 57 may be designed to correct myopia or hyperopia to emmetropia. Emmetropia is the state of vision in which a faraway object at infinity is in sharp focus with the eye lens in a neutral or relaxed state. Emmetropia may be in the range of +1 to −1 diopters.

In the embodiments, computer 30 may calculate the dimensions of protrusion 58 of central region 55 from information describing near-vision correction. In certain examples, the diameter of protrusion 58 is 0.5 to 4 millimeters (e.g., 0.5 to 1, 1 to 2, 2 to 3, and/or 3 to 4 millimeters), and the center of protrusion 58 has a thickness of 3 to 50 micrometers (e.g., 3 to 10, 10 to 20, 20 to 25, 25 to 30, 30 to 35, 35 to 40, and/or 40 to 50 micrometers). Generally, a protrusion 58 with a greater central thickness provides greater presbyopic correction. In an example, a protrusion 58 with a spherical shape, a diameter of 2 millimeters, and a central thickness of 30 micrometers adds a power of 2.5 to 4.0 diopters.

Figure 4:
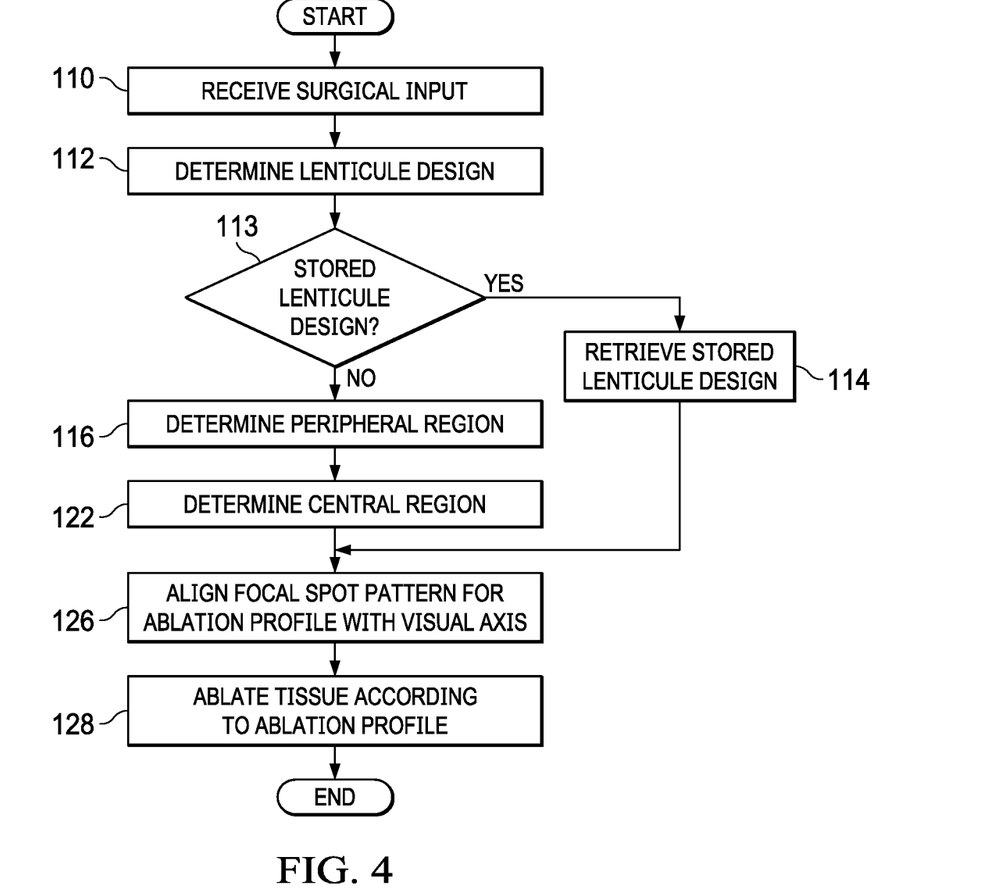
FIG. 4 illustrates a method for ablating a cornea of an eye that may be performed by the system of FIG. 1, according to certain embodiments.

FIG. 4 illustrates a method for ablating a cornea of an eye that may be performed by system 10 of FIG. 1, according to certain embodiments. The method starts at step 110, where computer 30 receives surgical input describing a surgical procedure. The surgical input may include information that computer 30 can use to retrieve or to calculate an ablation profile that describes the tissue to be removed. The surgical input may describe the patient's eye, e.g., the spherical error, cylinder error, axis of the cylinder error, added power (spherical error for reading distance correction), and/or x,y position of the visual axis.

Computer 30 determines the ablation profile from the surgical input at step 112. The ablation profile may be stored at step 113, or may need to be calculated. If the ablation profile is stored at step 113, the method proceeds to step 114, where computer 30 retrieves the stored ablation profile. Then the method proceeds to step 126, where computer 30 begins ablating the cornea.

If there is no stored ablation profile at step 113, the method proceeds to steps 116 to 122, where computer 30 calculates the ablation profile. Computer 30 determines the ablation profile for the peripheral region at step 116. In certain cases, the peripheral region may be designed to treat myopia, and the ablation profile may remove a thicker portion of material in the peripheral region towards the center. In other cases, the peripheral region may be designed to treat hyperopia, and the ablation profile may remove a thicker portion of material in the peripheral region towards the periphery. Computer 30 determines the ablation profile for the central region at step 122. The protrusion of the central region have any suitable shape and/or size. In certain examples, the diameter of the protrusion is 0.5 to 4 millimeters, and the center of the protrusion has a thickness of 3 to 50 micrometers.

At step 126, computer 30 aligns a focal spot pattern corresponding to the ablation profile with an axis (e.g., visual or optical) of the eye. In certain embodiments, computer 30 may determine a focal spot pattern corresponding to the ablation profile. Computer 30 may receive a measurement or coordinates identifying the location of the axis and then align the focal spot pattern with the axis. Computer 30 instructs controllable components to ablate the cornea according to the ablation profile at step 128. The method then ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for treating presbyopia, comprising:
a plurality of controllable components comprising:
a light source configured to generate a light beam; and
a scanner configured to direct a focal point of the light beam;
a computer configured to:
determine an ablation profile to remove tissue from a central region and a peripheral region of a cornea of a first eye of a pair of eyes, the ablation profile designed to remove tissue from the central region to yield a protrusion to provide for near-vision, the protrusion of the central region of the cornea having a diameter of 0.5 to 4 millimeters and a height of 3 to 50 micrometers, the ablation profile designed to remove tissue from the peripheral region to correct to emmetropia;
instruct one or more of the controllable components to ablate the cornea of the first eye according to the ablation profile;
determine a second ablation profile designed to correct a second eye of the pair of eyes to emmetropia; and
instruct one or more of the controllable components to ablate a second central region and a second peripheral region of the cornea of the second eye according to the second ablation profile to correct the second eye to emmetropia.

2. The ophthalmic surgical system of claim 1, wherein the protrusion is spherical.

3. The ophthalmic surgical system of claim 1, the protrusion has a height of 20 to 40 micrometers.

4. The ophthalmic surgical system of claim 1, the computer configured to determine the ablation profile to remove tissue from the central region and the peripheral region of the cornea of the first eye of the pair of eyes by:
determining the ablation profile is designed to treat myopia, the ablation profile removing a thicker portion of the cornea at an inner portion of the peripheral region than at an outer portion of the peripheral region.

5. The ophthalmic surgical system of claim 1, the computer configured to determine the ablation profile to remove tissue from the central region and the peripheral region of the cornea of the first eye of the pair of eyes by:
determining the ablation profile is designed to treat hyperopia, the ablation profile removing a thicker portion of the cornea at an outer portion of the peripheral region than at an inner portion of the peripheral region.

6. The ophthalmic surgical system of claim 1, wherein:
the first eye of the pair of eyes is non-dominant; and
the second eye of the pair of eyes is dominant.

7. The ophthalmic surgical system of claim 1, the computer further configured to:
generate a focal spot pattern corresponding to the ablation profile; and
align the focal spot pattern relative to a visual axis to ablate the cornea.

8. The ophthalmic surgical system of claim 1, the computer further configured to:
generate a focal spot pattern corresponding to the ablation profile, a point of the focal spot pattern designated to be aligned with a visual axis of the eye;
determine the visual axis of the eye; and
align the point of the focal spot pattern relative to the visual axis to ablate the cornea.

9. A method for treating presbyopia, comprising:
generating, by a light source of a plurality of controllable components, a light beam;
directing, by a scanner of the plurality of controllable components, a focal point of the light beam;
determining, by a computer, an ablation profile to remove tissue from a central region and a peripheral region of a cornea of a first eye of a pair of eyes, the ablation profile designed to remove tissue from the central region to yield a protrusion to provide for near-vision, the protrusion of the central region of the cornea having a diameter of 0.5 to 4 millimeters and a height of 3 to 50 micrometers, the ablation profile designed to remove tissue from the peripheral region to correct to emmetropia;

instructing, by the computer, one or more of the controllable components to ablate the cornea of the first eye according to the ablation profile;

determining, by the computer, a second ablation profile designed to correct a second eye of the pair of eyes to emmetropia; and instructing, by the computer, one or more of the controllable components to ablate a second central region and a second peripheral region of the cornea of the second eye according to the second ablation profile to correct the second eye to emmetropia.

10. The method of claim 9, wherein the protrusion is spherical.

11. The method of claim 9, the determining, by the computer, the ablation profile to remove tissue from the central region and the peripheral region of the cornea of the first eye of the pair of eyes comprises:

determining the ablation profile is designed to treat myopia, the ablation profile removing a thicker portion of the cornea at an inner portion of the peripheral region than at an outer portion of the peripheral region.

12. The method of claim 9, the determining, by the computer, the ablation profile to remove tissue from the central region and the peripheral region of the cornea of the first eye of the pair of eyes comprises:

determining the ablation profile is designed to treat hyperopia, the ablation profile removing a thicker portion of the cornea at an outer portion of the peripheral region than at an inner portion of the peripheral region.

13. The method of claim 9, wherein:
the first eye of the pair of eyes is non-dominant; and
the second eye of the pair of eyes is dominant.

14. The method of claim 9, further comprising:
generating, by the computer, a focal spot pattern corresponding to the ablation profile; and
aligning, by the computer, the focal spot pattern relative to a visual axis to ablate the cornea.

15. The method of claim 9, further comprising:
generating, by the computer, a focal spot pattern corresponding to the ablation profile, a point of the focal spot pattern designated to be aligned with a visual axis of the eye;
determining, by the computer, the visual axis of the eye; and
aligning, by the computer, the point of the focal spot pattern relative to the visual axis to ablate the cornea.

16. The method of claim 9, wherein the protrusion has a height of 30 to 50 micrometers.

17. An ophthalmic surgical system for treating presbyopia, comprising:
a plurality of controllable components comprising:
a light source configured to generate a light beam; and
a scanner configured to direct a focal point of the light beam;
a computer configured to:
determine an ablation profile to remove tissue from a central region and a peripheral region of a cornea of a first eye of a pair of eyes, the first eye of the pair of eyes is non-dominant, a second eye of the pair of eyes is dominant, the ablation profile designed to remove tissue from the central region to yield a protrusion to provide for near-vision, the protrusion of the central region of the cornea being spherical with a diameter of 0.5 to 4 millimeters and with a height of 30 to 50 micrometers, the ablation profile designed to remove tissue from the peripheral region to correct to emmetropia, the computer determining the ablation profile by:
determining the ablation profile is designed to treat myopia, the ablation profile removing a thicker portion of the cornea at an inner portion of the peripheral region than at an outer portion of the peripheral region; or
determining the ablation profile is designed to treat hyperopia, the ablation profile removing a thicker portion of the cornea at an outer portion of the peripheral region than at an inner portion of the peripheral region;
generate a focal spot pattern corresponding to the ablation profile, a point of the focal spot pattern designated to be aligned with a visual axis of the eye;
determine the visual axis of the eye;
align the point of the focal spot pattern relative to the visual axis to ablate the cornea;
instruct one or more of the controllable components to ablate the cornea of the first eye according to the ablation profile;
determine a second ablation profile designed to correct the second eye to emmetropia; and
instruct one or more of the controllable components to ablate a second central region and a second peripheral region of the cornea of the second eye according to the second ablation profile to correct the second eye to emmetropia.

18. The ophthalmic surgical system of claim 1, wherein the protrusion has a height of 30 to 50 micrometers.

\* \* \* \* \*